United States Patent [19]

Prior et al.

[11] 4,376,634
[45] Mar. 15, 1983

[54] ASSAY KIT HAVING SYRINGE, DILUTION DEVICE AND REAGENTS WITHIN SEALED CONTAINER

[75] Inventors: Richard B. Prior, Westerville; Vincent A. Spagna, Dublin, both of Ohio

[73] Assignee: Mallinckrodt, Inc., St. Louis, Mo.

[21] Appl. No.: 241,859

[22] Filed: Mar. 9, 1981

Related U.S. Application Data

[63] Continuation-in-part of Ser. No. 154,762, May 30, 1980, abandoned.

[51] Int. Cl.³ .......................................... G01N 33/50
[52] U.S. Cl. .................................. 436/502; 128/758; 128/759; 128/760; 128/765; 422/61; 435/292; 435/294; 435/295; 435/810
[58] Field of Search .............. 422/61; 435/292, 294, 435/295, 810; 23/230 B; 128/757, 758, 759, 760, 765

[56] References Cited

U.S. PATENT DOCUMENTS

| | | | |
|---|---|---|---|
| 3,039,938 | 6/1962 | Charm | 435/292 X |
| 3,045,494 | 7/1962 | Gerarde | 128/765 X |
| 3,045,494 | 7/1962 | Gerarde | 73/425.6 |
| 3,187,888 | 6/1965 | Corwin | 206/56 |
| 3,433,712 | 3/1969 | Gerarde | 435/292 |
| 3,449,081 | 6/1969 | Hughes | 422/61 |
| 3,783,106 | 1/1974 | Henshilwood | 128/759 X |
| 3,876,503 | 4/1975 | Mennen | 195/103.5 R |
| 3,883,396 | 5/1975 | Thomas, Jr. | 195/100 |
| 3,890,204 | 6/1975 | Avery | 128/759 X |
| 4,038,029 | 7/1977 | Teller | 23/230 B |

OTHER PUBLICATIONS

Limulus Amebocyte Lysate PYROGENT ®, Technical Product Data, Mallinckrodt, Inc., St. Louis, MO, May 1979.
P. Novotny et al., J. Med. Microbiol, 8, 413-427, (1975).
Unopette Test 5853, Information and Procedure Product Information, Becton, Dickinson, Rutherford, N.J., 1974.
Vincent A. Spagna et al., British Journal of Venereal Diseases, 35(3), 179-182, (1979).
Richard B. Prior et al., Journal of Clinical Microbiology, 10, 394-395, (1979).

*Primary Examiner*—Sidney Marantz
*Attorney, Agent, or Firm*—Bernard, Rothwell & Brown

[57] ABSTRACT

A diagnostic kit for rapid presumptive diagnosis of gonococcal urethritis using Limulus lysate reagent. A urethral specimen taken by a syringe without a needle is mixed with specimen diluent carried by a sterile reservoir containing the requisite amount of diluent. After a sufficient dilution has occurred, a needle is placed on the syringe permitting delivery to a vial containing the Limulus lysate reagent. After a specified incubation period the vial is observed for gelation as the presumptive diagnostic test for gonococcal urethritis.

42 Claims, 16 Drawing Figures

ASSAY KIT HAVING SYRINGE, DILUTION DEVICE AND REAGENTS WITHIN SEALED CONTAINER

This is a continuation in part of a prior application, Ser. No. 154,762 filed May 30, 1980, abandoned.

BACKGROUND AND DISCUSSION OF THE INVENTION

Levin and Bang first reported in 1964 that lysate made from the amebocytes of *Limulus polyphemus* (horseshoe crab) coagulated in the presence of bacterial endotoxin, and currently it has been improved to detect picogram ($10^{-12}$ grams) quantities of endotoxin. Due to its extreme sensitivity and specificity to endotoxins, the Limulus amebocyte lysate (LAL) assay has been employed to detect contaminating endotoxins in pharmaceuticals and parenteral drugs intended for human use. In addition, the LAL assay has been utilized clinically in the initial evaluation of meningitis, urinary tract infections, and urethritis-cervicitis syndromes.

The invention as described herein relates to a method and an apparatus for diagnostic assay or test of the existence of gonorrhea particularly in males. Although such tests have existed prior to the invention described herein, these tests, suffering under inadequacies as to their complexity, dependability, performance time, repeatability, have been expensive to prepare and of questionable accuracy. All of these tests have proved to require a substantial amount of time before accurate diagnosis can be made. With the method and apparatus described herein, many of these problems are overcome.

Both from the type of diagnostic employed as well as the apparatus used, the speed and accuracy of the test is enhanced. The assay used is a LAL assay which has been shown to be particularly effective in the rapid presumptive diagnosis of gonococcal urethritis in males. Tests employing Limulus lysate are explained in detail in the *British Journal of Venereal Diseases*, Volume 55, No. 3, 1979, pages 179-182. The culture predictability of *Neisseria gonorrhoeae* (sensitivity) was 100%, specificity was 96.3%, and the overall accuracy was 98%, indicating that the test offers a significant advancement in the area of diagnostic tests for gonorrhea.

The tests described in the *British Journal of Venereal Diseases* mentioned above are rather cumbersome and do not lend themselves to clinical evaluation where simplicity and speed are essential. For example, the original tests employed plastic test tubes and pipettes for qualitative evaluation of the clinical specimen. The preparation of test tubes, dilution, and the use of pipettes are not practical when used by the physician.

Rather, it is preferable that the various elements required in the diagnostic assay tests be packaged in a self-contained kit including a specimen collection apparatus, dilution device, and lysate assay material, such that the physician can use the assay immediately or a short period of time thereafter such as one-half hour. Diluting the specimen must be accomplished without contamination since the Limulus test detects picogram quantities of endotoxin. The device must also be simple and easy to use.

The invention relates to a method and apparatus which achieves the desired objectives discussed above in a unique manner which is efficient, simple, accurate and repeatable. More specifically, the apparatus relates to a kit which includes all the needed elements, including the solutions required for diluting a specimen and diagnosing the specimen after proper dilution, all without contamination. The elements of the kit include a sterile, non-pyrogenic syringe, such as a tuberculin syringe, with a cap, a sterile non-pyrogenic dilution container with a frangible closure, and a sterile non-pyrogenic needle with sheath or protector and a single test vial of Limulus lysate—lyophilized.

The syringe is initially used without the needle to take the specimen under partial vacuum when the plunger is pulled. Other items evaluated for the quantitative collection of urethral exudate have included microdiluter probes and capillary tubes. These have not been successful because the exudate is rather viscous requiring some kind of negative pressure to extract necessary amount of specimen for use in the diagnostic test. In addition, the pointed capillary tubes have the potential of harming the patient. Therefore, the tuberculin syringe without a needle has proved to be a preferable device to collect the urethral discharge under sufficient negative pressure and without potential injury to the patient while also maintaining good visibility during the collection operation.

The dilution step in the process must be accurate, quick, simple and inexpensive while avoiding the potential of contamination with respect to the specimen or creating a potential bio-hazard to the user. It is desirable that in diluting the specimen the system be sealed and remain sealed during mixing and dilution until the specimen is added to the lysate. The dilution device used is a container of diluent having a frangible closure. The device is specifically configured to cooperate with the syringe such that when the syringe is inserted into the dilution device, after the frangible closure is broken, a seal will be maintained between the two elements to permit dilution in a closed system and in a single step. The diluent used in the test herein is sterile, pyrogen-free water ($H_2O$), isotonic, pyrogen free solutions such as aqueous NaCl, etc.

The needle is then affixed to the syringe with the diluted specimen therein, and subsequently the needle, affixed to the syringe, is inserted into a vial septum and a measured portion of the diluted specimen is delivered to the LAL contained in the vial by pressing the plunger of the syringe.

In other embodiments the needle configuration is such that the needle may be placed on the syringe prior to dilution and enables the frangible closure to be broken by the needle as affixed to the syringe. This eliminates a separate element which may otherwise be required for breaking the frangible closure. In any event after the diluted specimen has been delivered to the vial, the specimen and LAL mixture after incubation for about 30 minutes is viewed to determine under observation whether gelation has occurred. Where there is gelation, the test presumptively indicates the presence of *N.gonorrhoeae*.

In taking specimen for the presumptive test in conjunction with diagnosis of gonococcal and nongonococcal cervicitis in females, there are additional problems in actually obtaining the specimen from the cervical os. In the laboratory the samples can be collected using a pipette with a gentle aspiration and subsequently diluting the sample in pyrogen-free water. Although these methods are acceptable and produce a high degree of sensitivity and specificity (Spagna et al., American Journal of Obstetrics and Gynecology, Vol. 137, No. 5, Pages 595-599, 1980), this approach is not practical for the practicing physician. Problems accompanying the use of the pipette occur because of the location of the cervix and the varying consistency and tenacity of the exudate. In addition, a series of dilution steps required would increase the possibility of error and of contamination to the sample and to the person actually employing the apparatus for taking the sample since the sample may contain biohazards. The invention is directed to overcoming these problems and arriving at a self-contained collection-dilution device which can be used by the physician at the patient's side. The device, as with the kit for the male presumptive diagnosis, includes the materials for collection of the specimen from the endocervix, for dilution of the specimen and for the subsequent LAL assay using a single-test lysate vial.

An aspiration step may be employed for the female where the specimen is aspirated in excess of the quantity needed and is subsequently delivered to or transferred to a syringe assembly which is then affixed to the diluent reservoir. This approach however requires several steps, and aspiration of the exudate from the endocervix, although possible, should be avoided, because it requires additional manipulation, is prone to errors and contamination with exogenous endotoxins. Acceptance of such a meticulous method by practicing physicians is difficult.

It is desirable to arrive at a method which avoids the problems above and is one which the physician is familiar with and can use quickly and accurately for rapid dilution and ease of operation. One procedure which is familiar to physicians in collecting endocervical samples and involves little or no risk to the patient is the use of a cotton tip swab. The swab is inserted into the cervical os about one to two centimeters. Although cotton is preferred since it is wettable, pyrogen-free polyester swabs or other devices might work, but the absorbent cotton should collect more endotoxins. Once the sample is obtained on the cotton tip the sample is diluted and subsequently delivered to LAL assay for determining the presumptive presence of N.gonorrhoeae.

The above discussion of the background of the invention and elements of the apparatus and the method for taking the diagnostic assay are only general in nature. A more detailed discussion of the elements of the invention as well as the details of its operation in connection with the method are described in a description of the preferred embodiment hereafter.

DETAILED DESCRIPTION OF THE PREFERRED EMBODIMENT

Figure 1:
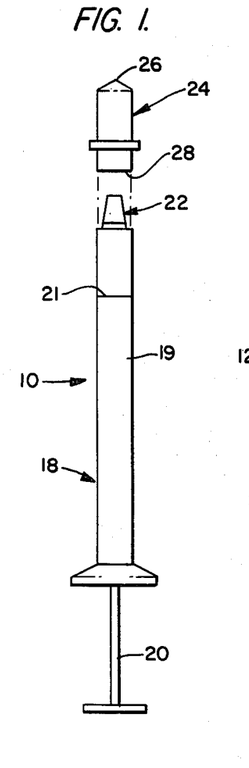
FIG. 1 is an elevation view of the sterile syringe with cap.

The elements which form the kit for use in making the diagnostic test, as shown in FIGS. 1, 2, 3 and 4, include a syringe assembly 10, a dilution device 12, a needle assembly 14, and vial 16. Syringe assembly 10 as shown in FIG. 1 is a non-pyrogenic 1 cc syringe 18 with a cap 24. It is preferable to employ a plastic disposable device to assure the pyrogen-free state of the syringe. Syringe 18 includes hollow body portion 19 and tip 22. A mark 21 is made on syringe body 19 to indicate a 0.25 cc volume defined by the cavity from the tip to the mark within the syringe. Tip 22 of the syringe is conical shaped and is usually covered with a cap 24. Preferably the cap 24 has a closed pointed end 26 and an open end 28 for covering the tip 22 of syringe 18.

Figure 2:
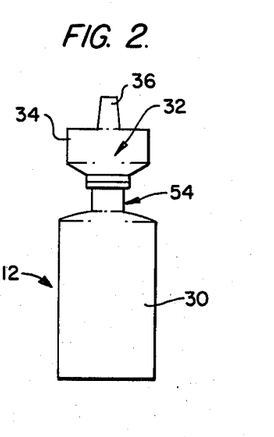
FIG. 2 is an elevation view of the sterile dilution device with closure.

Dilution device 12, as shown in FIG. 2, is a sterile, nonpyrogenic 20 cc device including a flexible, plastic container 30 with a closure 32 which is sealed to the container with a frangible seal readily broken by twisting the closure from the container. The fluid carried in container 30 is sterile, pyrogen free $H_2O$ or other acceptable aqueous solution. Closure 32 has a flange portion 34 for gripping by the user to twist it from container 30. A cone member 36 extends from the upper portion of flange portion 34 remote from the top of container 30 and is configured to fit into an opening or channel of the container 30 which will be discussed in more detail later.

Although a 20 ml device is shown, the size of the container is variable with quantity of specimen collected and the sensitivity of the assay. For example the container should be sufficient in volume capacity to contain about 5-20 ml of diluent, preferably about 0.5-10 ml for LAL sensitivity of 0.25-0.5 ng/ml EC-2 reference endotoxin.

Figure 3:
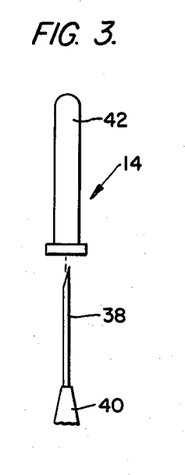
FIG. 3 is an elevation view of a sterile needle with sheath.

Needle assembly 14 includes needle 38 with adapter 40 at one end for affixing the needle by a force fit to the tip 22 of syringe 18. Preferably needle assembly 14 includes a sterile, non-pyrogenic 23 G one-inch needle 38 with protector 42. The protector is a plastic cylindrical device which force fits with adapter 40 to cover the needle 38.

Figure 4:
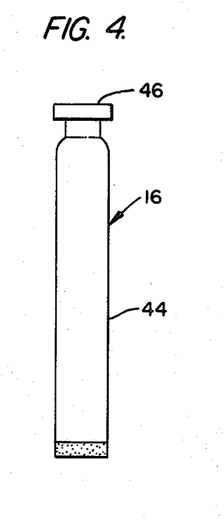
FIG. 4 is a single test vial of the Limulus amebocyte lysate (LAL)-lyophilized.

Vial 16 is a glass tube having a standard septum top 46 which can be penetrated by the syringe needle 38. In this case, as shown in FIG. 4, vial 16 contains the Limulus Amebocyte Lysate (LAL)-Lyophilized.

Figure 5:
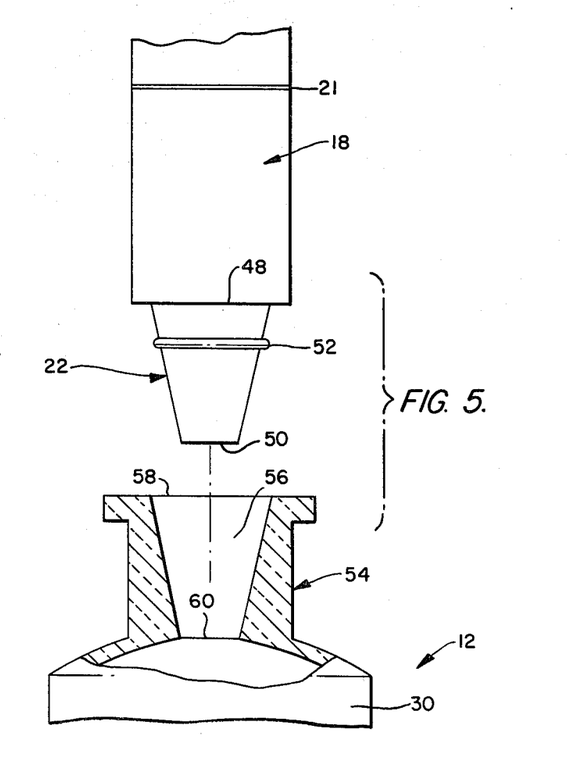
FIG. 5 is an enlarged view and elevation of the tip of the syringe shown in FIG. 1 with the neck portion of the dilution device shown in FIG. 2.

As can be seen in FIG. 5 the tip 22 and dilution device 12 are specially configured to insure a firm fit therebetween. Tip 22 is cone shaped in configuration with the base 48 being secured to the syringe and the cone top 50 being of a smaller diameter than base 48 to facilitate insertion into the dilution device 12. Circumscribing tip 22 is a ridge 52 for enhancing the seal between the syringe and the dilution device 12 when the tip and dilution device are fitted together. The dilution device 12 defines a neck portion 54 extending upwardly therefrom with a channel 56 therethrough configured to be substantially identical with the exterior configuration with tip 22 except for the ridge 52. Specifically, the channel 56 includes an upper opening 58 whose diameter is substantially identical to or slightly smaller that of cone base 48 of tip 22 and a lower opening 60 whose diameter is substantially identical or slightly smaller to that of cone top 50. In this way the channel 56 provides a complementary surface for fitting over tip 22 of the syringe to maintain a seal between the syringe and container during dilution of the specimen. The dilution operation will be explained later in the description of the preferred embodiment.

In testing for gonorrhea using Limulus lysate, it has been found that for a sensitivity of about 0.25 ng/ml EC-2, reference endotoxin standard, a sample dilution of about 1:400 will differentiate between gonococcal and nongonococcal disease. This dilution was determined by clinical tests and from these data an expression can be made as follows:

$$C.D. = k/\text{Lysate sensitivity (ng/ml EC-2)}$$

where
  C.D. = critical dilution of urethral sample (±one two-fold)
  k = 100 (A constant determined by clinical tests)

A positive Limulus test equal to or greater than the critical dilution indicates gonococcal urethritis while a negative Limulus test indicates nongonococcal urethritis. For example, a 0.025 ml ± 0.01 ml exudate specimen would require a diluent reservoir to contain about 10 ml of water to yield an average dilution ratio of 1:400 which would be appropriate for a lysate sensitivity of 0.25 ng/ml EC-2.

Given the dimensions of the syringe it can be determined by mathematical formula the exact level within the syringe to which the specimen should be drawn for obtaining the 0.025 cc volume of specimen.

The diluted specimen is then delivered to a vial containing lysate which is subsequently incubated and observed for gelation. This procedure, as explained in connection with the article in the *British Journal of Venereal Diseases* proved to be successful as a diagnostic test and a significant advancement in this area.

Figure 6:
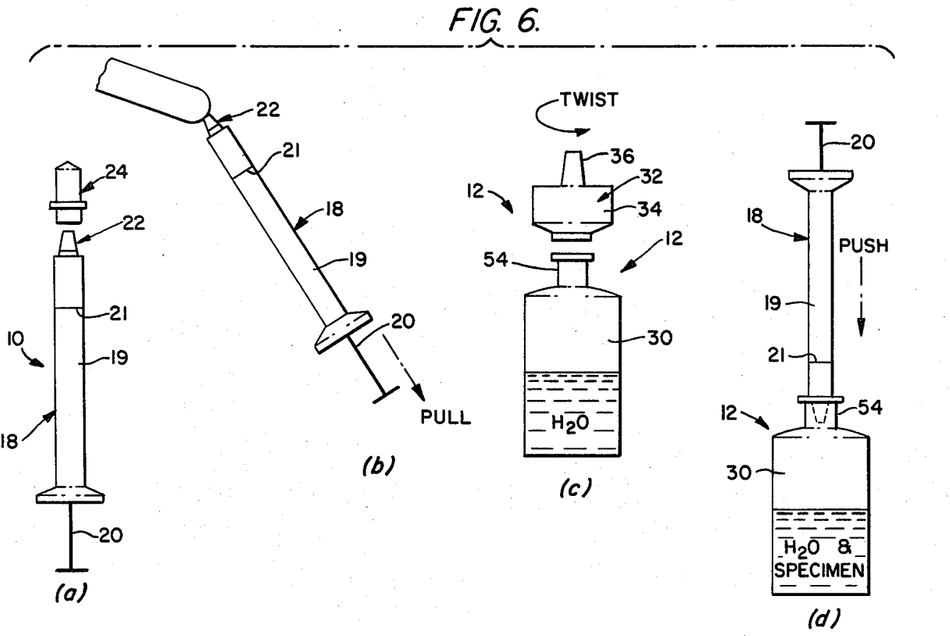
FIG. 6 shows the operation of various elements shown in FIGS. 1-5 in steps (a)-(d) of the process of taking and diluting the specimen.

When using the elements as shown in the figures and described hereinafter, the simplicity and reliability of the test are ones which make it amenable as a single diagnostic test which can be performed quickly and accurately by the physician. More specifically, the sterile nonpyrogenic 1-cc syringe 18 is employed as an element for taking the sample or specimen of exudate from the urethra, typically of a male, as shown in FIG. 6. For a 0.025 cc sample, a mark 52 is made on the syringe so that the operator can readily determine when a sufficient sample or specimen has been obtained.

The syringe 18 normally comes with a cap 24 to protect tip 22 of the syringe from contamination until the cap is removed for taking of the specimen. As can be seen in steps (a)-(d) of FIG. 6, after cap 24 is removed tip 22 of syringe 18 is located adjacent the area where the specimen is located. Plunger 20 is then pulled to draw the specimen into syringe 18 up to the 0.025 cc mark 52. A margin for error of 0.025 cc ± 0.01 cc is allowed. At this stage a sufficient sample has been drawn into syringe 18 by the negative pressure caused by the pulling of the plunger. This sample is diluted in subsequent steps before it is added to the Limulus lysate.

Diluent is carried in a sterile, nonpyrogenic dilution device 12 having closure 32 which can be seen in FIG. 2. This dilution device 12 contains sterile, pryrogen-free water ($H_2O$) for diluting the specimen. This particular dilution device includes a frangible closure which seals the diluent in the container until the seal is broken. To gain access to the diluent for the specimen, as can be seen in step (c) of FIG. 6, the closure 32 is twisted off by grasping flange 34 to break the seal and allow the closure 32 to be removed. The syringe tip 22 is then pressed into neck 54 of the device 12 such that the specimen can be expelled into device 12 for dilution purposes. As shown in FIG. 5 both the internal surfaces of the channel 56 and external surfaces of tip 22 of syringe 18 are configured to maintain a seal between the syringe and the dilution device during the specimen dilution process. In this manner the dilution step can be accomplished without contaminating the exudate obtained during the collection of the specimen or the operator with the sample which may contain bio-hazard agents.

Referring now to step (d) of FIG. 6, plunger 20 is pressed carefully to expel the exudate into the container. Device 12 is then inverted while maintained in the assembled disposition with syringe 18 to continue the diluting process. This is accomplished by moving plunger 20 of the syringe 18 up and down about five times as shown in step (e) of FIG. 7 together with vigorous shaking. After sufficient mixing has been obtained, plunger 20 is pulled downwardly as shown in step (f) of FIG. 7 to fill the syringe to the 0.25 cc mark 21 with diluted specimen. After device 12 has been inverted syringe 18 is then removed with a slight twist-pull motion from dilution device 12 with the diluted specimen as shown in step (g). This should be done without touching the syringe tip 22. A stopper is then placed in the dilution device by inserting the cone 36 of the closure 32 into the neck 54 of the device as shown in step (h) of FIG. 7.

The vial containing the LAL, as shown in FIG. 4, typically has an elastic seal or septum 46 which is configured to be penetrated by syringe needle 38 while maintaining a seal. This septum 46 comes with a dust cover which is not shown in Figures herewith. After the requisite amount of diluted specimen has been drawn into syringe 18, needle 38 in the protector 42 is placed on the syringe 18 by securely pushing it straight onto tip 22. The friction generated between the adapter 40 on needle 38 and the tip of the syringe is sufficient to maintain the needle on the syringe during delivery of exudate to the LAL vial. As this is a standard procedure in the medical and diagnostic field further details as to the manner in which the needle is attached to the syringe would simply be redundant and unnecessary for those skilled in the art. Once the needle is in place as can be seen in step (i) of FIG. 8 the protector 42 is pulled straight off, step (j), to expose the needle for use in delivering the specimen.

Figure 8:
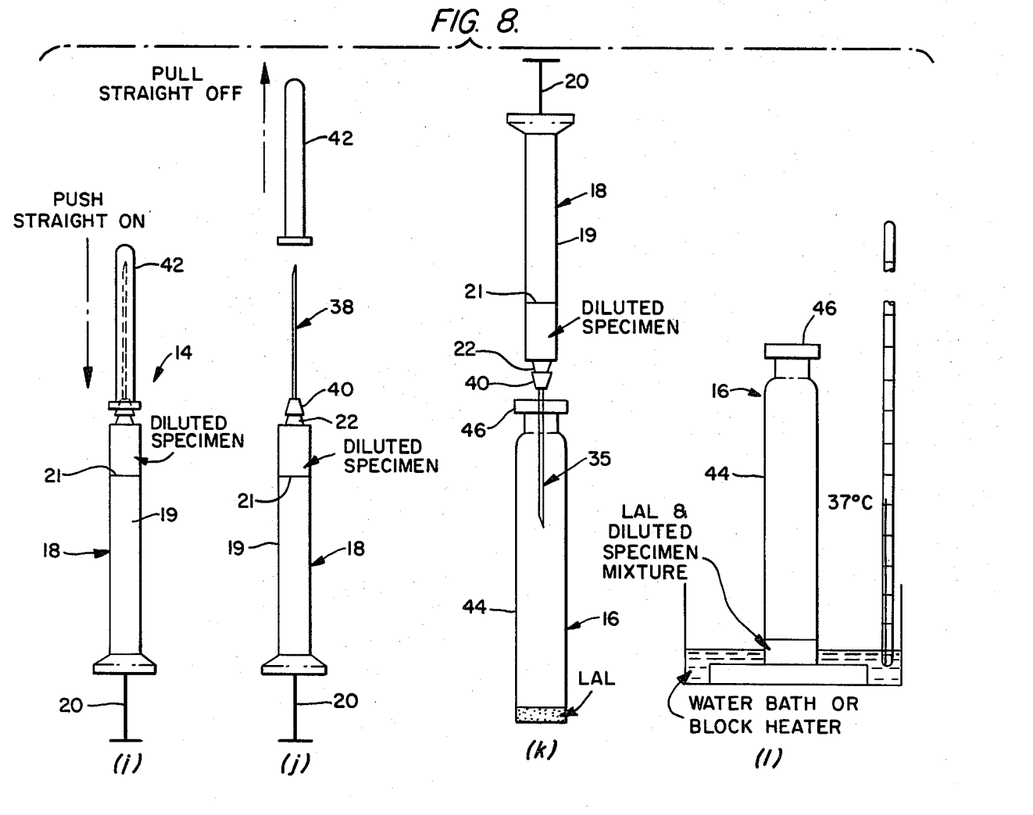
FIG. 8 relates to steps (i)-(l) in delivering the specimen as diluted to the LAL vial.

In step (k) vial 44 with the LAL is shown with the dust cover having been removed. The needle 38 is inserted, after attachment to syringe 10, into vial septum 46, and dilute specimen is expelled into the vial by pushing downwardly on plunger 20. The needle and syringe assembly is then removed and discarded. The vial 44 containing the LAL and specimen mixture should be swirled gently to insure good mixture of these elements, and mixture in vial 44 is then incubated for about 30 minutes at about 37° C. undisturbed as shown in step (l). After this specified incubation, if gelation is observed by inverting the tube, there is an indication of the presence of *N.gonorrhoeae.*

Figure 7:
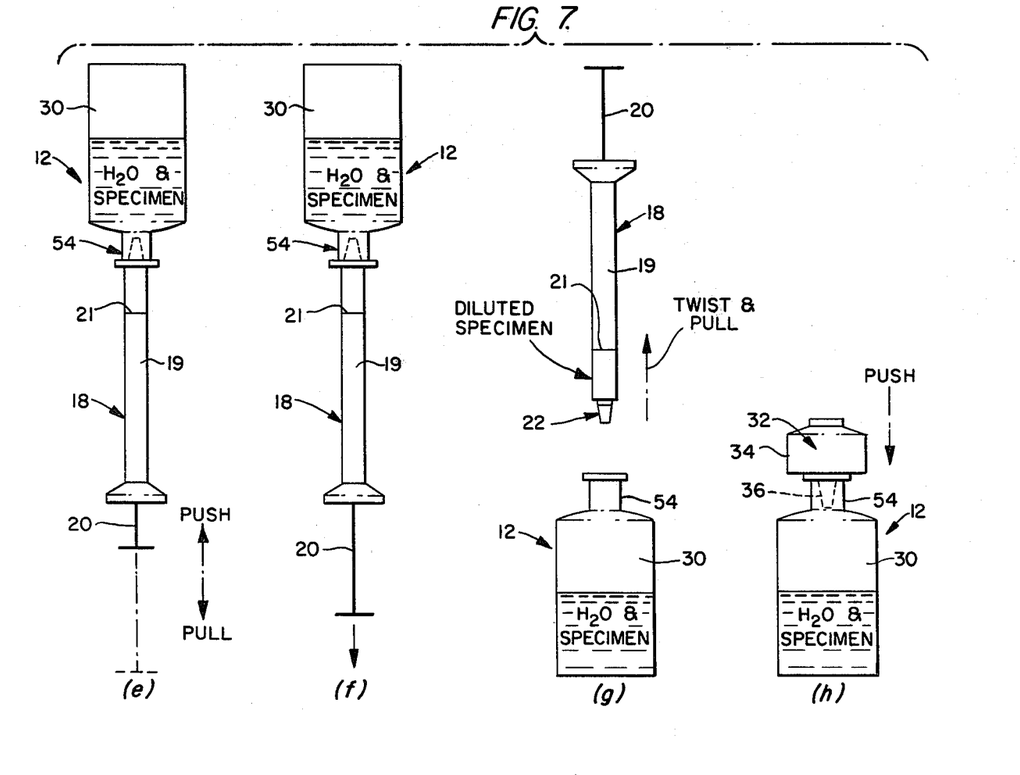
FIG. 7 shows steps (e)-(h) further relating to dilution of the specimen.

The kit for performing this diagnostic test should include all the elements as shown in FIGS. 1–4 and operated in connection with the steps as shown in FIGS. 6–8. However, these are only representative of the preferred embodiment for making the diagnostic tests. Other devices may be used so long as they can perform the various steps of specimen taking, dilution, and diagnosis while free from contamination.

Figure 9:
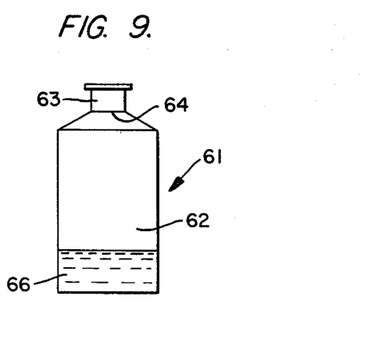
FIG. 9 shows an alternative sterile dilution device.
Figure 10:
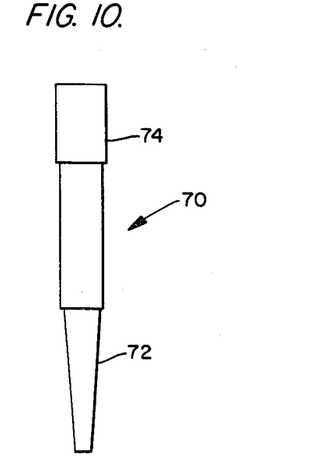
FIG. 10 shows an element for breaking the seal in the device of FIG. 9.

As shown in FIGS. 9 and 10 alternative elements can be used for the dilution device as well as an element for breaking seal. In FIG. 9 the dilution device 61 includes a container or bottom portion 62 generally cylindrical in configuration having a conical portion connecting neck 63 to the bottom portion 62. Between the neck 63 and the bottom portion 62 is a frangible seal or membrane 64 to seal the liquid diluent 66 contained in container 62 until the seal is broken by plunger 70 as shown in FIG. 10. Plunger 70 includes a nozzle or pointed end 72 and a tubular portion 74 which enables plunger 70 to be held by the user and forced through the opening in neck 63 to break the seal 64. Once the seal is broken the diluent is mixed with the sample collected in the syringe as described in connection with FIGS. 1 through 8 as discussed above. The internal diameter of the neck 63 cooperates with the tip of the syringe to provide a seal between the syringe and container 62 during the dilution step of the test. Furthermore, the seal 64 actually provides a snap lock such that when the user presses tip 22 of the syringe into neck 63 of the container 62 a snap will occur indicating that the syringe has been pressed to a desired extent and that a seal is obtained between membrane 64 and the syringe tip 22. In this manner pyrogens are not permitted to enter the diluting process, and the diluting step is completed in a pyrogen free atmosphere. This avoids bio-hazards to the user as well as enhances the predictability of the test. Otherwise where pyrogens or other endotoxins are allowed to enter the system, the test may create a false positive situation.

In operation using these alternative elements as shown in FIGS. 9 and 10, once the sample has been obtained using the syringe as described above, the plunger is grasped by the user and the pointed end 72 is pressed into neck 63 of device 61 to break the frangible seal between the neck and the diluent contained therein. Once the seal is broken the plunger 70 is withdrawn and the tip of the syringe is inserted into the neck until the snap of the snap lock mechanism is felt by the operator. The plunger is then moved in and out to dilute the specimen as discussed above in connection with the other dilution device. After sufficient dilution a requisite amount of diluted specimen is withdrawn from the container by moving the plunger downwardly the syringe is subsequently removed and the remaining steps for taking the test are the same as those discussed earlier. Alternatively, the syringe cap 24 is configured to not only cover tip 22, but also break seal in lieu of plunger 70. In addition, such a cap could be used to seal the device 61 after the specimen has been diluted and the syringe withdrawn.

Features of the invention as described above not only facilitate qualitative testing but also make quantitative testing easier and more simple as well. For example a pipette tip such as a 0.05 ml tip can be placed over dilution device opening and 0.05 ml diluted specimen can be delivered to a micro-dilution plate for end point determinations. In operation the pipette tip would simply be affixed to the neck 54 of the device 12 containing diluted sample, and the device 12 would then be inverted and squeezed to place a drop (0.05 ml) in a microdilution plate for serial two fold dilutions and subsequent end point determinations of endotoxin in the sample (see *Journal of Clinical Microbiology,* Vol. 10, pp. 394–395, 1979).

The use of the single test vial in specimen collection dilution kit is more for qualitative testing, has the advantage of simplicity, and is the preferred method to be used by physicians in clinics. The use of microdilution material is more for quantitative studies and is useful in evaluating lysate lots and determining breakpoints. Thus, the kit described above not only has advantages for qualitative testing at the patient's side, but it has quantitative uses as well.

Figures 11, 12:
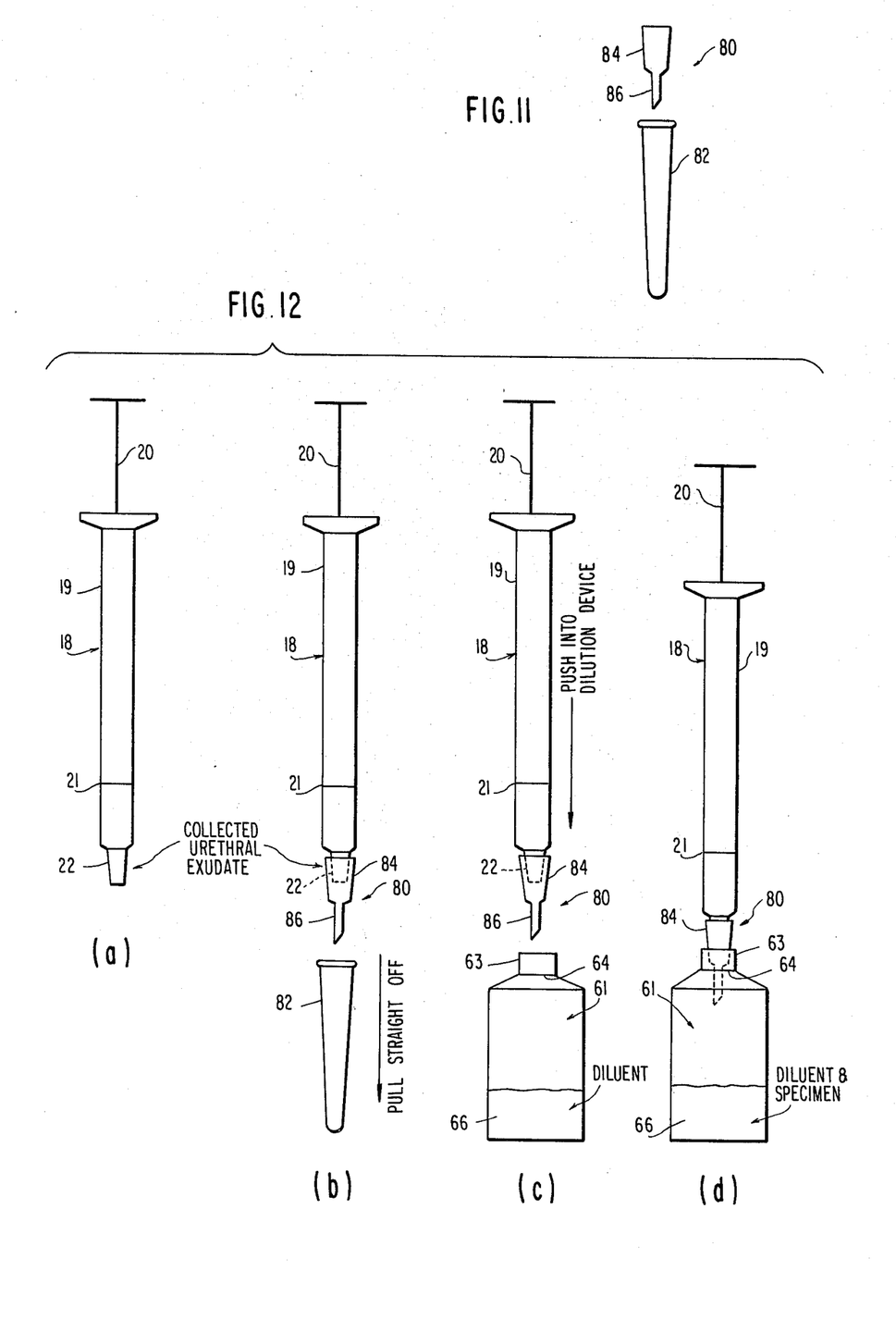
FIG. 11 shows an alternative needle assembly.
FIG. 12 relates to steps (a)-(d) for diluting a specimen, employing the needle assembly of FIG. 11.

In FIG. 11 there is shown a device adapted to be used in conjunction with the syringe as shown in FIGS. 1–10 which eliminates two steps in the diagnostic test described in the previous figures. This device when secured to tip 22 of syringe 18 provides a means for breaking the seal or closure of a container as well as providing a means for access through the septum of vial such as vial 44.

This device includes a plastic needle of relatively short length but relatively large diameter when compared with the needle 38 as shown in FIG. 3. Needle assembly 80 includes needle 86 and sheath 82. Specifically, needle 86 is one-half inch, large 8–16 g, sterile, non-pyrogenic plastic needle with a luer fitting 84 at one end of the needle to accommodate syringe tip 22. A protective sheath 82 fits over the needle 86 in the manner similar to that of sheath 42 and needle 38. Needle assembly 14 as shown in FIG. 3 and a plunger as shown in FIG. 10.

The operation of this needle assembly 80 in conjunction with the specific steps for taking the diagnostic test is similar to that described above with respect to FIGS. 1–10 except that the step of employing a separate element for breaking the frangible membrane in the dilution reservoir or devices is eliminated. In view of this similarity only a few steps using the needle assembly 80 will be described, but it shall be understood that the remaining steps not described are identical to those already discussed above. In this manner a large amount of redundancy which would otherwise occur is substantially eliminated.

In the specimen collecting step needle assembly 80 is affixed to the specimen collecting syringe 18 immediately following the collection of exudate from the patient and will remain affixed to the syringe throughout the dilution in the diluent reservoir and addition of sample to the LAL vial. The steps employing the needle assembly 80 will be more clearly understood in connection with the items shown in FIG. 12. Here following the collection of urethral exudate, the needle assembly 80 with the protective sheath covering the needle is attached to the tip 22 of the syringe 18. The protective sheath is then removed as can be seen in step (b) of FIG. 12 leaving the needle 86 secured to the tip 22. The exposed needle 86 is then inserted into dilution device 12 with the needle breaking frangible membrane 64 sealing the diluent 66 within the device 61 as can be seen in steps (c) and (d). The needle 86 is forced through membrane 64 sufficiently to engage and seal external surfaces of needle 86 with the membrane 64 and external surface 84 with internal surfaces of container neck 63 during the dilution step. The remaining steps in mixing are the same as those shown in FIGS. 7(e) and (f).

Figure 13:
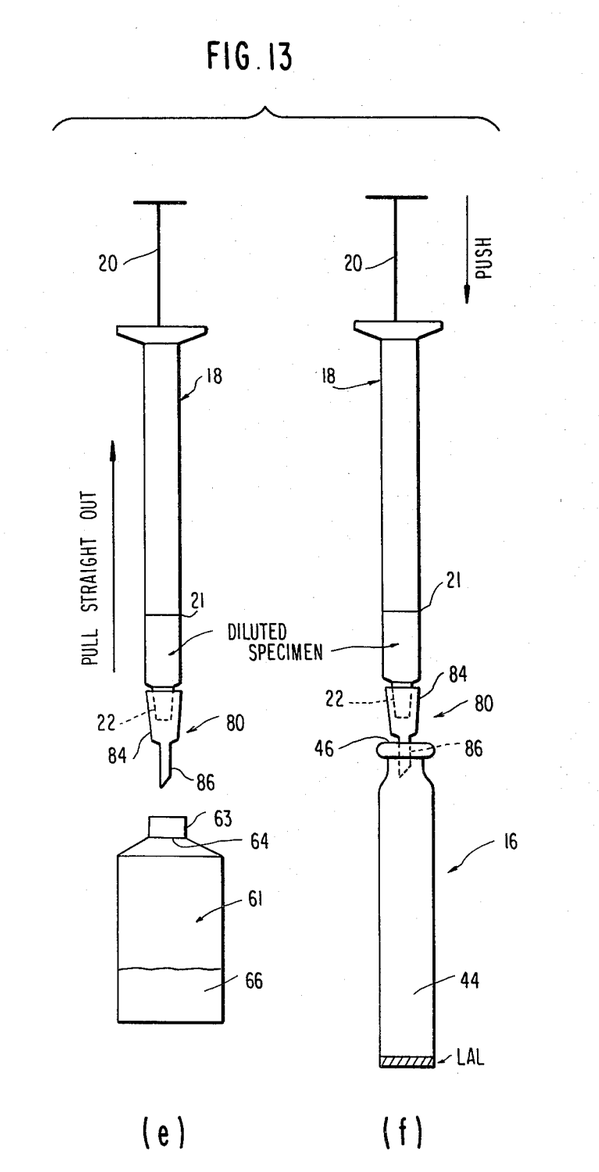
FIG. 13 relates to steps (e) and (f) employing the needle assembly of FIG. 11 and delivering a diluted specimen to an LAL vial.

Once the dilution step has been completed, as can be seen in FIG. 13, the syringe containing a 0.25 ml of diluted specimen is removed from the dilution reservoir as can be seen in step (e) of FIG. 13. Subsequently, the needle 86 is inserted into LAL vial through the septum 46 where the diluted specimen is delivered to the LAL within the vial as shown in FIG. 13(f). The incubation steps are identical to those as described before. From steps employing the device it can be seen that the use of the larger plastic needle assembly 80 eliminates the separate step of breaking the frangible seal of reservoir 61 before a needle assembly is placed on the tip 22 of syringe 18. The elimination of this step of course enhances the speed and accuracy of the test and even further reduces the possibility of contaminating the specimen during the diagnostic test.

The above has been a discussion of a kit and procedure for rapid presumptive diagnosis of a urethral specimen taking from a male. Certain features are readily adaptable for testing the female; however, the specimen preferably should be obtained in a different manner. Rather than simply drawing the specimen into a syringe, a swab device is employed on which a specimen can be absorbed and removed from within the cervical os. The following is a discussion of the elements used in conjunction with taking the specimen from the female and subjecting the specimen to dilution and ultimately to an assay as has been done in conjunction with the presumptive diagnosis for the male.

Figure 14:
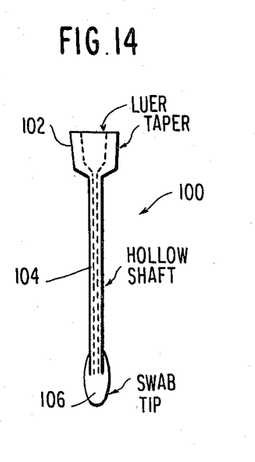
FIG. 14 shows a swab assembly for taking the specimen.

Swab assembly 100 as shown in FIG. 14 is used in conjunction with the syringe assembly 18 for taking the specimen. The swab assembly 100 includes a swab tip 106 which is depyrogenated cotton or other absorbent pad material supported on one end of shaft 104 which has a length of about between 3-7 cm. Base 102 located on the other end of shaft 104 is a plastic luer fitting having tapered surfaces on the outside for attachment to a dilution reservoir and also on the inside for attachment to syringe tip 22. The shaft is hollow throughout its entire length and open at each end to communicate the swab tip 106 with the base 102. Dilution device 108 has a length to accommodate the full length of swab assembly 100 when inserted through mouth 105.

Figure 15:
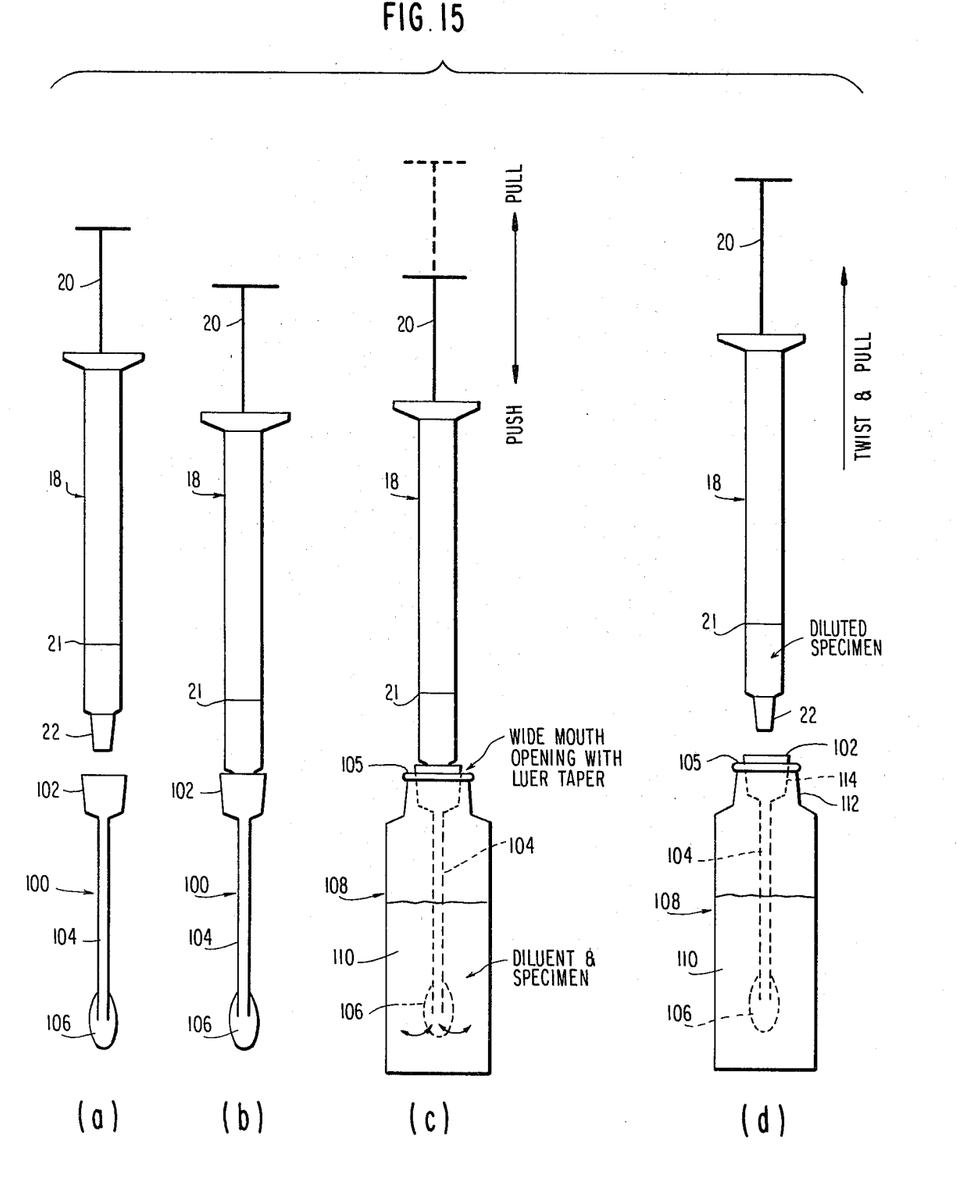
FIG. 15 relates to steps (a)-(d) for diluting a specimen, employing the swab assembly of FIG. 14.

The operation of the swab assembly 100 can be more clearly appreciated in conjunction with FIG. 15. Before taking the specimen, assembly 100 is fitted onto tip 22 of syringe 18 and assembled as shown in step (b). The luer surfaces of base 102 and tip 22 cooperate to retain assembly 100 on the syringe assembly 18 by a friction fit. To obtain a sample the tip of swab assembly 100 is inserted into the cervical os about one (1) to two (2) centimeters and withdrawn. After the sample is obtained it is diluted in dilution device 108. This is accomplished by initially breaking a frangible seal which covers the opening of dilution device 108 having a diluent 110 therein. The dilution device or reservoir 108 has a larger opening and neck portion 114, than that described in FIGS. 2 and 5, to allow the swab tip to pass into the reservoir and accommodate base 102 of the swab assembly 100. As can be seen in step (c) of FIG. 15 the swab assembly is inserted through the broken frangible seal into the dilution reservoir 108 until the luer fitting 102 forms a seal with the mouth 105 of the reservoir 108. Mixing is accomplished by push-pull action on the plunger 20 to force the diluent in and out of the syringe assembly 18 through the swab tip 106. Following adequate mixing, the syringe plunger 20 is operated to draw into the syringe 0.25 ml of diluted specimen after which the syringe 18 is removed from the swab assembly 100 leaving the swab assembly attached to the dilution reservoir 108 as can be seen in step (d). The remaining steps for the assay are identical to those described in FIG. 8, steps (i), (j), (k) and (l) where a needle is placed on tip 22 of the syringe and the diluted specimen is then subsequently delivered to the LAL vial and incubated as described before.

Figure 16A:
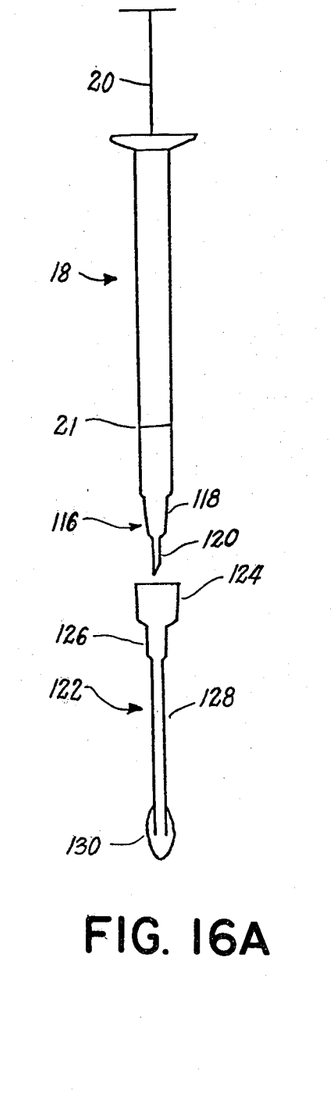
FIG. 16 relates to steps (a) and (b) which show another embodiment of a syringe and swab assembly.
Figure 16B:
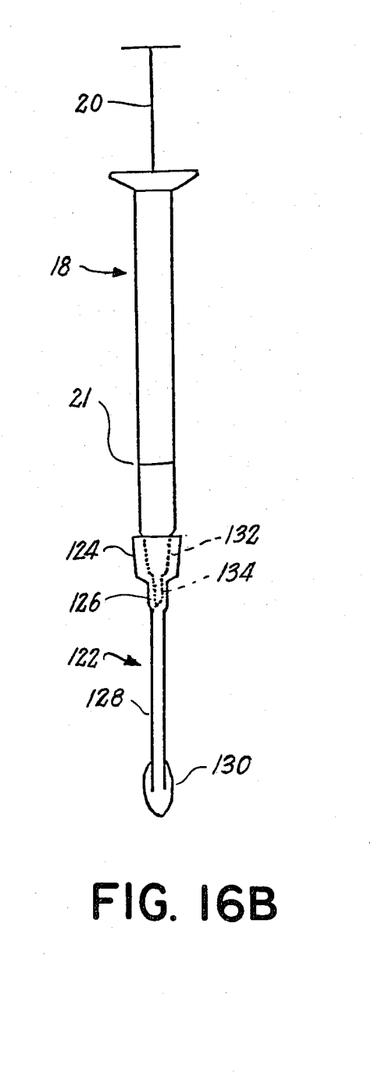

In FIG. 16 there is shown another device for the female assay kit which eliminates the need for a separate needle 14 in FIG. 3 or FIG. 11. The syringe is made with the short needle already attached which, after the dilution step, is used to penetrate the rubber septum as shown in FIG. 13(f). The syringe assembly 18 has a tip 116 which includes a larger needle 120 similar to needle 86 in FIG. 13 but formed integrally with syringe assembly 18. Intermediate needle 120 and the remainder of the syringe assembly is a luer shaped base portion 118 having a configuration similar to luer fitting of tip 22. The swab assembly 122 is configured to cooperate with the syringe 18 such that the base 124 of the swab assembly can accommodate the configuration of the tip 116 as shown in FIG. 16(b). In other words the base 124 is configured internally at 132 to receive both the needle and luer shaped portion 118 of the tip 116 in sealing relationship therewith. The remainder of the assembly 122, substantially identical to that of assembly 100 shown and discussed in connection with FIG. 14, includes hollow shaft 128 having at the end opposite the base 124 a cotton tip 130.

In taking a sample the swab assembly 122 is placed on the tip 116 in a manner similar to that described in conjunction with FIG. 15. After the sample is taken from the cervical os and diluted as before and once the swab assembly has been removed, the syringe can be used to deliver the diluted specimen to the LAL vial by simply puncturing the septum as described in FIG. 13(f) for the male assembly. The swab assembly 122 can be delivered to the kit already assembled to the syringe such that there is no preassembly required before the specimen is taken. This eliminates the step of inserting the syringe into the swab assembly and the consequential risk of contamination.

The data indicate that the diluent volume for the female assay will be about between 5 and 30 ml of water for lysate with the minimum sensitivity of about 0.25 ng/ml EC-2 and may contain a dispersing agent such as about a 5% solution of Pyrosperse.

The swab tips as mentioned above should be depyrogenated to insure that the swabs are all endotoxin free at the level of sensitivity tested. This depyrogenation can be obtained by heating the swabs to a relatively high temperature over a period of time. For example, heating the swabs to about 200° C. for about one-half hour produces swabs which are substantially endotoxin free for the level of sensitivity being tested at the LAL. Other means, of course, can be employed for this purpose, such as cobalt radiation or ethylene oxide.

The apparatus employing the swab assembly and the sealed dilution system as discussed above can also be used for male patients in those situations where there is not enough urethral exudate to be tested by the method described earlier in this specification. In this situation, although the swab assembly such as the one shown in FIG. 15 could be employed, normally the size of the cotton tip would be reduced with the tip being placed on the end of the shaft similar in size to a 21 to 23 gauge one-inch needle. The dilution reservoir as well as the fill volume would also be reduced. Otherwise except for actually taking the specimen, all the steps in performing the diagnostic test would be identical to those described above for the female.

We claim:

1. A diagnostic kit comprising
   (a) a syringe having a tip with an opening for extracting a specimen to be tested under negative pressure and expelling said specimen under positive pressure;
   (b) a sealed dilution device containing a preselected quantity of sterile, pyrogen-free diluent for diluting said specimen, said dilution device having an opening for providing access to said sterile, pyrogen-free diluent;
   (c) a needle fixable to the tip of said syringe; and
   (d) a vial containing reagents for an assay, said vial having a septum penetrable by said needle;
   wherein said tip is engageable with said dilution device for receiving sterile, pyrogen-free diluent from said dilution device and said needle is of a sufficient length to pass through said septum and provide a path to said reagents for an assay contained in said vial for diluted specimen.

2. The kit according to claim 1 wherein said reagents for an assay comprise a material for detecting venereal disease.

3. The kit according to claim 2 wherein said reagents for an assay includes LAL for detecting gonoccocal and non-gonoccocal urethritis or cervicitis.

4. The kit according to claim 3 wherein the tip of said syringe is a truncated cone with the base of the cone being adjacent the remainder of the syringe and the top of the cone being exposed for insertion into the dilution device, the opening in the dilution device having a complementary conical surface for engaging the tip of said syringe to provide a seal between the syringe and the dilution device as the specimen is expelled into and withdrawn from the dilution device.

5. The kit according to claim 4 wherein said tip includes a ridge substantially circumscribing said cone for engaging the surface of said dilution device defining said opening to seal said dilution device with said syringe.

6. The kit according to claim 5 wherein said dilution device is a sterile, non-pyrogenic container containing sterile pyrogen-free $H_2O$, said syringe is a sterile, non-pyrogenic 1 cc. syringe, the needle is a sterile, non-pyrogenic 23 G 1 inch needle, and the vial contains lyophilized Limulus amebocyte lysate.

7. A method for diagnostic test comprising:
   (a) taking a specimen of the material to be tested with a syringe having an end portion for placing in the area where the specimen exists and a plunger portion for imparting a negative or positive pressure, pulling said plunger to impart negative pressure to draw a specimen into said syringe;
   (b) providing a preselected amount of sterile, pyrogen-free diluent in a container which has an opening for access to the container and a closure for sealing said opening;
   (c) removing said closure to expose said opening within said container;
   (d) placing said end portion of said syringe with the specimen therein into said opening with sufficient force to seal the path between the sterile, pyrogen-free diluent container and the syringe, diluting the specimen by expelling the specimen into the sterile, pyrogen-free diluent container and withdrawing the diluted specimen into the syringe, removing the syringe from the sterile, pyrogen-free diluent container, with a selected amount of diluted specimen in said syringe;
   (e) placing a needle on the end portion of the syringe;
   (f) providing in a vial reagents for an assay for diagnosing the specimen, said vial having a septum portion penetrable by said needle;
   (g) pushing said needle through said septum and expelling said diluted specimen into said vial by pressing said plunger downwardly and providing positive pressure on the specimen; and
   (h) observing said specimen and reagents for an assay for a signal to indicate positive or negative results.

8. The method according to claim 7 wherein said sterile, pyrogen-free diluent is sealed within said container, said closure is fixed to said container by frangible seal, wherein said removal step includes twisting said closure to break said frangible seal for exposing said opening and providing access to said sterile, pyrogen-free diluent.

9. The method according to claim 8 wherein said step of providing sterile, pyrogen-free diluent includes providing a sufficient amount of sterile, pyrogen-free diluent to dilute said specimen to about a ratio of 1 to 400.

10. The method according to claim 9 wherein said dilution step includes arranging said container in an upright position, placing said end portion of the syringe into the opening of said container and expelling the specimen into the container by pushing the plunger downwardly, inverting the assembled syringe and said container and mixing the liquids by moving the plunger of the syringe up and down, pulling the plunger until a selected amount of diluted specimen is drawn into the syringe from the container, inverting the assembly again and withdrawing the filled syringe by drawing it straight up without touching the syringe tip.

11. A diagnostic kit comprising:
    (a) a specimen-collecting means for extracting exudate under negative pressure and expelling said specimen under positive pressure;
    (b) a sealed dilution device including a container containing a preselected quantity of sterile, pyrogen-free diluent for diluting said specimen, said dilution device having an opening for providing access to said sterile, pyrogen-free diluent; and
    (c) a vial containing reagents for an assay having a resealable opening configured to receive the diluted specimen in sealed relationship with said specimen-collecting means for sealing the diluted specimen and reagents for the assay from the surrounding atmosphere;
   wherein said dilution device opening has a frangible seal sealing said sterile, pyrogen-free diluent within said container and said specimen-collecting means is configured to engage said dilution device in sealed relationship therewith at said dilution device opening to receive said sterile, pyrogen-free diluent from said container sealed from the surrounding atmosphere.

12. The diagnostic kit according to claim 11 wherein said specimen collecting means includes an elongated hollow body, a plunger moveable within said body, said body portion having a tip at one end with an opening for collecting said specimen under negative pressure and expelling said specimen under positive pressure, said body portion having another end through which extends said plunger for actuation by an operator toward said one end to provide positive pressure to expel said specimen and away from said one end to provide negative pressure.

13. The diagnostic kit according to claim 11 or 12 including a needle for being secured to the tip of said hollow body of said specimen collecting means, said vial having a septum for sealing relationship with said needle when penetrated by the needle such that the collected diluted specimen can be expelled within said vial after having penetrated the septum in sealing relationship therewith.

14. A method for diagnostic test comprising:
(a) taking a specimen of material to be tested under negative pressure;
(b) providing a preselected amount of sterile, pyrogen-free diluent in a container which has an opening for access sealed by a frangible membrane;
(c) breaking said frangible membrane to obtain access to the sterile, pyrogen-free diluent within said container;
(d) diluting the specimen by expelling the specimen under positive pressure through said opening and in sealed relationship with said membrane to seal the path for the specimen from the surrounding atmosphere;
(e) withdrawing a preselected amount of diluted specimen from said container while sealed from the surrounding atmosphere;
(f) providing in a vial reagents for an assay for diagnosing a specimen, said vial having a resealable opening for receiving diluted specimens;
(g) delivering the diluted specimen to said vial in sealed relationship with said resealable opening and expelling said diluted specimen into said vial sealed from the surrounding atmosphere; and
(h) observing said specimen and reagents for an assay for a signal to detect positive or negative results.

15. The method according to claim 14 wherein said steps for collecting specimen under negative pressure and expelling specimen under positive pressure include providing an elongated hollow body with a plunger therein moveable within said body portion and having one end open for collecting and expelling said specimen and another end from which extends said plunger for operation by user whereby pressing of said plunger towards said one end provides positive pressure for expelling specimen and retracting of said plunger toward the other end provides negative pressure for collecting a specimen.

16. The method according to claim 15 wherein said hollow body includes a tip for penetrating said container, said frangible membrane extending across the opening, said diluting step including, after breaking said frangible membrane, extending said tip into said opening for engagement by said broken membrane to provide a seal between the hollow body and the container while diluting said specimen.

17. The method according to claim 16 wherein said step of providing sterile, pyrogen-free diluent includes providing a sufficient amount of sterile, pyrogen-free diluent to dilute said specimen to a ratio of about 1 to 400.

18. A diagnostic kit comprising:
(a) a specimen-collecting means including a body for extracting exudate under negative pressure and expelling said specimen under positive pressure;
(b) a hollow shaft having at one end a base for releasably securing said shaft to said body and having at the other end an absorbent pad for absorbing the specimen;
(c) a sealed dilution device including a container containing a preselected quantity of sterile, pyrogen-free diluent for diluting said specimen, said dilution device having an opening for providing access to said sterile, pyrogen-free diluent;
(d) a frangible seal for covering said opening and sealing said sterile, pyrogen-free diluent within said container;
(e) said specimen-collecting means being configured to engage said dilution device in sealed relationship therewith at said opening to receive sterile, pyrogen-free diluent from said container sealed from surrounding atmosphere; and
(f) a vial containing reagents for an assay, said vial having a resealable opening configured to receive diluted specimen in sealed relationship with said specimen-collecting means for sealing the diluted specimen and reagents for the assay from surrounding atmosphere.

19. The kit according to claim 18 wherein said base is configured for engagement with said dilution device in sealed relationship therewith.

20. The kit according to claim 19 wherein said dilution device is sufficiently long to accommodate the entire length of said shaft within said dilution device when the shaft base is in sealing relationship therewith.

21. The kit according to claim 20 wherein said absorbent pad is a cotton tip covering the other end of said shaft for forcing fluid entering and leaving the hollow shaft through the cotton tip.

22. The kit according to claim 21 wherein such shaft and tip comprise a depyrogenated cotton swab and have a length between about 3 to 7 cm.

23. The diagnostic kit according to claim 22 wherein said body is elongated and hollow, a plunger moveable within said body, said body having at one end an opening for collecting said specimen under negative pressure and expelling said specimen under positive pressure, said body having another end through which extends said plunger for actuation by an operator toward said one end to provide positive pressure to expel said specimen and away from said one end to provide negative pressure and said base configured for being releasably secured to said body.

24. The diagnostic kit according to claim 23 wherein said elongated, hollow body includes a tip at said one end of said body and a needle for being secured to tip on said body of said specimen collecting means, said vial having a septum for sealing relationship with said needle when penetrated by the needle such that the collected diluted specimen can be expelled within said vial after having penetrated the septum in sealing relationship therewith.

25. The diagnostic kit according to claim 24 wherein said dilution device includes a neck portion of reduced diameter relative to said container, said neck portion having internal surfaces defining an opening, said opening being sealed by a frangible membrane.

26. A diagnostic kit comprising:
(a) a syringe having a tip with an opening for drawing therethrough a specimen to be tested under negative pressure and expelling therethrough said specimen under positive pressure;
(b) a hollow shaft having at one end a base for releasably securing said shaft to said tip of the syringe and having at the other end an absorbent pad for absorbing the specimen;
(c) a sealed dilution device for containing a preselected quantity of sterile, pyrogen-free diluent for diluting said specimen, said dilution device having an opening for providing access to said sterile, pyrogen-free diluent;
(d) a needle affixable to the tip of said syringe; and
(e) a vial containing reagents for an assay, said vial having a septum penetrable by said needle;
wherein said base of said shaft is engageable with said dilution device for extending said shaft into said dilution device to provide a path through the pad and hollow shaft for sterile, pyrogen-free diluent contained in said dilution device and said needle is of a sufficient length to pass through said septum and provide a path to said reagents for an assay contained in said vial for diluted specimen.

27. The kit according to claim 26 wherein the tip of said syringe is a truncated cone with the base of the cone being adjacent the remainder of the syringe and the other end of the cone being exposed for insertion into the adapter of the needle base, the opening in the dilution device having a complementary conical surface for engaging the needle base as affixed to said syringe to provide a seal between the syringe and the dilution device as the specimen is expelled into and withdrawn from the dilution device.

28. The kit according to claim 27 wherein said adapter includes internal luer surfaces for friction fitting to said tip and external luer surfaces for friction fitting with said dilution device.

29. The kit according to claim 26 wherein said reagents for an assay comprise a material for detecting venereal disease.

30. The kit according to claim 29 wherein said reagents for an assay includes LAL for detecting gonoccocal and non-gonoccocal urethritis or cervicitis.

31. The kit according to claim 30 wherein said needle includes an adapter for securing the needle to said syringe and the tip of said syringe is a truncated cone with the base of the cone being adjacent the remainder of the syringe and the other end of the cone being exposed for insertion into the adapter of the needle, the opening in the dilution device having a complementary conical surface for engaging the needle base as affixed to said syringe to provide a seal between the syringe and the dilution device as the specimen is expelled into and withdrawn from the device.

32. A diagnostic kit comprising:
(a) a specimen-collecting means for obtaining a specimen and subjecting the specimen alternately to negative pressure and positive pressure;
(b) a sealed dilution device including a container containing a preselected quantity of sterile, pyrogen-free diluent for diluting said specimen, said dilution device having an opening for providing access to said sterile, pyrogen-free diluent;
(c) said opening having a frangible seal sealing said sterile, pyrogen-free diluent within said container;
(d) a needle having a base member for securing said needle to said specimen-collecting means, said base member being configured for engaging said dilution device in sealed relationship therewith at said opening to permit passage of sterile, pyrogen-free diluent from said container into said collecting means sealed from surrounding atmosphere; and
(e) a vial containing reagents for an assay, said vial having a resealable opening for sealing relationship with said needle when penetrated thereby to expel diluted specimen into said vial.

33. The diagnostic kit according to claim 32 wherein said specimen collecting means includes an elongated hollow body, a plunger moveable within said body, said body portion having a tip at one end with an opening for collecting said specimen under negative pressure and expelling said specimen under positive pressure, said body portion having another end through which extends said plunger for actuation by an operator toward said one end to provide positive pressure to expel said specimen and away from said one end to provide negative pressure and said needle base having means for being affixable to said tip.

34. A diagnostic kit comprising:
(a) a specimen-collecting means including a hollow body for extracting exudate under negative pressure and expelling said specimen under positive pressure;
(b) a hollow shaft having at one end a base for releasably securing said shaft to said body and having at the other end an absorbent pad for absorbing the specimen;
(c) a sealed dilution device including a container containing a preselected quantity of sterile, pyrogen-free diluent for diluting said specimen, said dilution device having an opening for providing access to said sterile, pyrogen-free diluent; and
(d) a vial containing reagents for an assay;
wherein said opening has a frangible seal sealing said sterile, pyrogen-free diluent within said container, said specimen-collecting means is configured to engage said dilution device in sealed relationship therewith at said opening to receive sterile, pyrogen-free diluent from said container sealed from surrounding atmosphere, said body of the specimen-collecting means has a tip at one end thereof and a needle for being secured to said tip of said specimen-collecting means, said vial has a septum for sealing relationship with said needle when penetrated by the needle such that the collected diluted specimen can be expelled within said vial after having penetrated the septum in sealing relationship therewith, and said needle has an adapter on one end thereof for securing said needle to said hollow body, said base of said hollow shaft is configured for releasably securing said shaft to said adapter.

35. The kit according to claim 34 wherein said adapter is integral with said hollow body.

36. The kit according to claim 35 wherein said adapter includes external luer surfaces and said base of the shaft includes internal luer surfaces for friction fitting to said external surfaces of said adapter and external luer surfaces to engage said dilution device in sealed relationship therewith.

37. The kit according to claim 36 wherein said base includes a hollow portion of intermediate diameter, to accommodate said needle, between a hollow portion of larger diameter, to accommodate said adapter, and said hollow shaft of smaller diameter.

38. A method for diagnostic test comprising:
(a) taking a specimen of material to be tested under negative pressure;
(b) providing a preselected amount of sterile, pyrogen-free diluent in a container which has an opening for access sealed by a frangible membrane;
(c) breaking said frangible membrane to obtain access to the sterile, pyrogen-free diluent within said container;
(d) diluting the specimen by expelling the specimen under positive pressure through said opening and in sealed relationship with said membrane to seal the path for the specimen from the surrounding atmosphere;
(e) withdrawing a preselected amount of diluted specimen from said container while sealed from the surrounding atmosphere;
(f) providing in a vial reagents for an assay for diagnosing a specimen, said vial having a resealable opening for receiving diluted specimen;
(g) delivering the diluted specimen to said vial in sealed relationship with said resealable opening and expelling said diluted specimen into said vial sealed from the surrounding atmosphere;
(h) observing said specimen and reagents for an assay for a signal to detect positive or negative results;
(i) said steps for collecting specimen under negative pressure and expelling specimen under positive pressure include providing an elongated hollow body with a plunger therein movable within said body portion and having one end open for collecting and expelling said specimen and another end from which extends said plunger for operation by user whereby pressing of said plunger towards said one end provides positive pressure for expelling specimen and retracting of said plunger toward the other end provides negative pressure for collecting a specimen; and
(j) said hollow body including a tip, a needle is affixed to the tip prior to breaking the frangible membrane, and the frangible membrane being broken by inserting the needle into the opening for the sterile, pyrogen-free diluent container.

39. The method according to claim 38 wherein the needle includes a base portion and the diluting step is accomplished in sealed relationship by pressing the base portion of the needle into sealing engagement with the internal surface of the opening to seal the path for the diluted specimen from the surrounding atmosphere.

40. A method for diagnostic test comprising:
(a) taking a specimen of material to be tested by absorbing the specimen on an absorbent pad located on the end of a hollow shaft;
(b) providing a preselected amount of sterile, pyrogen-free diluent in a container which has an opening for access sealed by a frangible membrane;
(c) breaking the frangible membrane to obtain access to the sterile, pyrogen-free diluent within said container;
(d) diluting the specimen by inserting the absorbent pad into the sterile, pyrogen-free diluent container and drawing sterile, pyrogen-free diluent under negative pressure through the pad and expelling drawn sterile, pyrogen-free diluent under positive pressure through the pad to the container while sealed from the surrounding atmosphere;
(e) withdrawing a preselected amount of diluted specimen from said container while sealed from the surrounding atmosphere;
(f) providing in a vial reagents for an assay for diagnosing a specimen, said vial having a releasable opening for receiving diluted specimen;
(g) delivering the diluted specimen to said vial in sealed relationship with said resealable opening and expelling said diluted specimen into said vial sealed from the surrounding atmosphere; and
(h) observing said specimen and reagents for an assay for a signal to detect positive or negative results.

41. The method according to claim 40 wherein said steps for drawing sterile, pyrogen-free diluent under negative pressure and expelling diluted specimen under positive pressure include providing an elongated hollow body with a plunger therein movable within said body and having one end open for collecting and expelling said specimen and another end from which extends said plunger for operation by user whereby pressing of said plunger towards said one end provides positive pressure for expelling specimen and retracting said plunger toward the other end provides negative pressure for drawing the sterile, pyrogen-free diluent.

42. The method according to claim 41 wherein said hollow shaft includes a base portion for sharing shaft to said hollow body, said frangible membrane extending across the opening, said diluting step including, after breaking said frangible membrane, extending said shaft into said opening for engagement of said container opening by said base portion to provide a seal between the hollow body and the container while diluting said specimen.

* * * * *

UNITED STATES PATENT AND TRADEMARK OFFICE
CERTIFICATE OF CORRECTION

PATENT NO. : 4,376,634

DATED : March 15, 1983

INVENTOR(S) : Richard B. Prior and Vincent A. Spagna

It is certified that error appears in the above-identified patent and that said Letters Patent is hereby corrected as shown below:

In the drawings, sheet 3, Fig. 8(K), delete the reference numeral "35" and substitute --38-- therefor.

Signed and Sealed this

Tenth Day of May 1983

[SEAL]

Attest:

GERALD J. MOSSINGHOFF

*Attesting Officer*     *Commissioner of Patents and Trademarks*

UNITED STATES PATENT OFFICE
CERTIFICATE OF CORRECTION

Patent No. 4,376,634          Dated March 15, 1983

Inventor(s) Richard B. Prior and Vincent A. Spagna

It is certified that error appears in the above-identified patent and that said Letters Patent are hereby corrected as shown below:

Column 2, line 16, after the word "extract", insert --the--.

Column 8, line 41, after the word "assembly", insert --80 can replace needle assembly--.

Column 18, line 22, "releasable" should be --resealable--.

Signed and Sealed this

Twenty-fourth Day of May 1983

[SEAL]

Attest:

DONALD J. QUIGG

Attesting Officer     Acting Commissioner of Patents and Trademarks